(12) United States Patent
Kato et al.

(10) Patent No.: US 6,419,818 B2
(45) Date of Patent: Jul. 16, 2002

(54) $NO_X$ CONCENTRATION-MEASURING METHOD

(75) Inventors: Nobuhide Kato, Aichi -Pref; Kunihiko Nakagaki, Nagoya; Satoshi Nishikawa, Chita, all of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/212,491

(22) Filed: Dec. 17, 1998

(30) Foreign Application Priority Data

Dec. 22, 1997 (JP) .............................. 9-353738

(51) Int. Cl.$^7$ ............................................ G01N 27/407
(52) U.S. Cl. ........................ 205/781; 204/425; 204/426
(58) Field of Search ................. 204/402, 421, 204/429, 781

(56) References Cited

U.S. PATENT DOCUMENTS

| | | | |
|---|---|---|---|
| 3,843,400 A | * 10/1974 | Radford et al. ............. 204/421 |
| 4,395,319 A | * 7/1983 | Torisu et al. | |
| 4,595,485 A | * 6/1986 | Takahashi et al. | |
| 4,927,517 A | * 5/1990 | Mizutani et al. ............ 204/425 |
| 5,476,001 A | 12/1995 | Hoetzel et al. | |
| 5,672,811 A | 9/1997 | Kato et al. | |
| 5,763,763 A | 6/1998 | Kato et al. | |

FOREIGN PATENT DOCUMENTS

| | | |
|---|---|---|
| EP | 0 769 693 | 4/1997 |
| EP | 0 810 433 | 12/1997 |
| JP | 08-271476 | 10/1996 |
| JP | 9-113484 | 5/1997 |

* cited by examiner

Primary Examiner—T. Tung
(74) Attorney, Agent, or Firm—Burr & Brown

(57) ABSTRACT

Disclosed is a NOx sensor for measuring a NOx concentration comprising a main pumping cell and a detecting electrode, the main pumping cell including an electrode (an inner pumping electrode and an outer pumping electrode) having no decomposing/reducing ability for NOx or a low decomposing/reducing ability for NOx, to be used so that an oxygen concentration in a measurement gas is controlled to have a predetermined value at which NO is not substantially decomposable, and the detecting electrode having a certain decomposing/reducing ability for NOx or a high decomposing/reducing ability for NOx, to be used so that NOx is decomposed to measure the NOx concentration by measuring an amount of oxygen produced during this process, wherein a cermet electrode composed of a Pt—Rh alloy and a ceramic component is used as the detecting electrode. Accordingly, it is possible to suppress the oxidation of Rh and the reconversion into the metal contained in the detecting electrode, stabilize the impedance, and stabilize the sensitivity to NOx.

1 Claim, 5 Drawing Sheets

$NO_x$ CONCENTRATION-MEASURING METHOD

BACKGROUND OF THE INVENTION

1. Field of the Invention

The present invention relates to a NOx concentration-measuring apparatus for measuring NOx contained in, for example, atmospheric air and exhaust gas discharged from vehicles or automobiles.

2. Description of the Related Art

Conventionally, those known as the method for measuring NOx in a measurement gas such as combustion gas include a technique in which the NOx-reducing ability of Rh is utilized to use a sensor comprising a Pt electrode and an Rh electrode formed on an oxygen ion-conductive solid electrolyte such as zirconia so that an electromotive force generated between both electrodes is measured.

However, the sensor as described above suffers the following problem. That is, the electromotive force is greatly changed depending on the change in concentration of oxygen contained in the combustion gas as the measurement gas. Moreover, the change in electromotive force is small with respect to the change in concentration of NOx. For this reason, the conventional sensor tends to suffer influence of noise.

Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform measurement for a combustion gas produced under such a combustion condition.

In order to solve the problems as described above, for example, Japanese Laid-Open Patent Publication No. 8-271476 discloses a NOx sensor comprising pumping electrodes having different NOx-decomposing abilities arranged in a first internal space which communicates with a measurement gas-existing space and in a second internal space which communicates with the first internal space, and a method for measuring the NOx concentration in which the $O_2$ concentration is adjusted by using a first pumping cell arranged in the first internal space, and NO is decomposed by using a decomposing pumping cell arranged in the second internal space so that the NOx concentration is measured on the basis of a pumping current flowing through the decomposing pump.

Further, Japanese Laid-Open Patent Publication No. 9-113484 discloses a sensor element comprising an auxiliary pumping electrode arranged in a second internal space so that the oxygen concentration in the second internal space is controlled to be constant even when the oxygen concentration is suddenly changed.

A cermet electrode composed of $Rh/ZrO_2$ is used for the NOx-decomposing electrode as described above. When the cermet electrode composed of $Rh/ZrO_2$ is used for the NOx-decomposing electrode, a phenomenon has been observed, in which the sensitivity is lowered in accordance with the increase in operating time. This phenomenon is caused by the increase in impedance of the decomposing pumping cell. When the NOx sensor element, in which the impedance has been increased, is observed, it has been found that the contact area is decreased between the NOx-decomposing electrode and the $ZrO_2$ substrate. In other words, it is postulated that the increase in impedance is caused by the decrease in contact area between the NOx-decomposing electrode and the $ZrO_2$ substrate.

It is postulated that the decrease in contact area between the NOx-decomposing electrode and the $ZrO_2$ substrate is caused by any change in volume, which is brought about by the oxidation ($Rh_2O_3$) of the metal Rh contained in the NOx-decomposing electrode and the reconversion of the oxidized product into the metal.

SUMMARY OF THE INVENTION

The present invention has been made taking the foregoing problems into consideration, an object of which is to provide a NOx concentration-measuring apparatus which makes it possible to suppress the oxidation of Rh and the reconversion into the metal contained in a NOx-decomposing electrode, stabilize the impedance, and stabilize the measurement sensitivity.

The present invention lies in a NOx concentration-measuring apparatus for measuring a NOx concentration, comprising an oxygen pump and a NOx-decomposing electrode, the oxygen pump including an electrode having no decomposing/reducing ability for NOx or a low decomposing/reducing ability for NOx, to be used so that an oxygen concentration in a measurement gas is controlled to have a predetermined value at which NO is not substantially decomposable, and the NOx-decomposing electrode having a certain decomposing/reducing ability for NOx or a high decomposing/reducing ability for NOx, to be used so that NOx is decomposed to measure the NOx concentration by measuring an amount of oxygen produced during this process, wherein a cermet electrode composed of a Pt—Rh alloy and a ceramic component is used as the NOx-decomposing electrode.

The use of the cermet electrode composed of the Pt—Rh alloy and the ceramic component, as the NOx-decomposing electrode suppresses the oxidation of Rh and the reconversion of the oxidized product into the metal contained in the NOx-decomposing electrode. Even when the operating time is increased, it is possible to avoid the occurrence of the increase in impedance which would be otherwise caused by the decrease in contact area between the NOx-decomposing electrode and the substrate. That is, when the NOx concentration-measuring apparatus according to the present invention is used, the impedance is stabilized, and it is possible to stabilize the measurement sensitivity as well.

It is appropriate that a weight ratio of Rh in the Pt—Rh alloy contained in the NOx-decomposing electrode is more than 0% by weight and not more than 90% by weight.

Specifically, a ratio of Pt to Rh in the NOx-decomposing electrode is preferably Pt:Rh=10:90 to 99:1 as represented by a weight ratio. It is especially desirable that the weight ratio of Pt in the Pt—Rh alloy contained in the NOx-decomposing electrode is not less than 25% by weight, and Pt is not contained in an amount of 100% by weight. It is more preferable that the ratio of Pt to Rh in the NOx-decomposing electrode is Pt:Rh=25:75 to 75:25 as represented by a weight ratio.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Explanation will be made below with reference to FIGS. 1 to 6 for illustrative embodiments of the NOx concentration-measuring apparatus according to the present invention (hereinafter simply referred to as "NOx sensor according to the embodiment").

Figure 1:
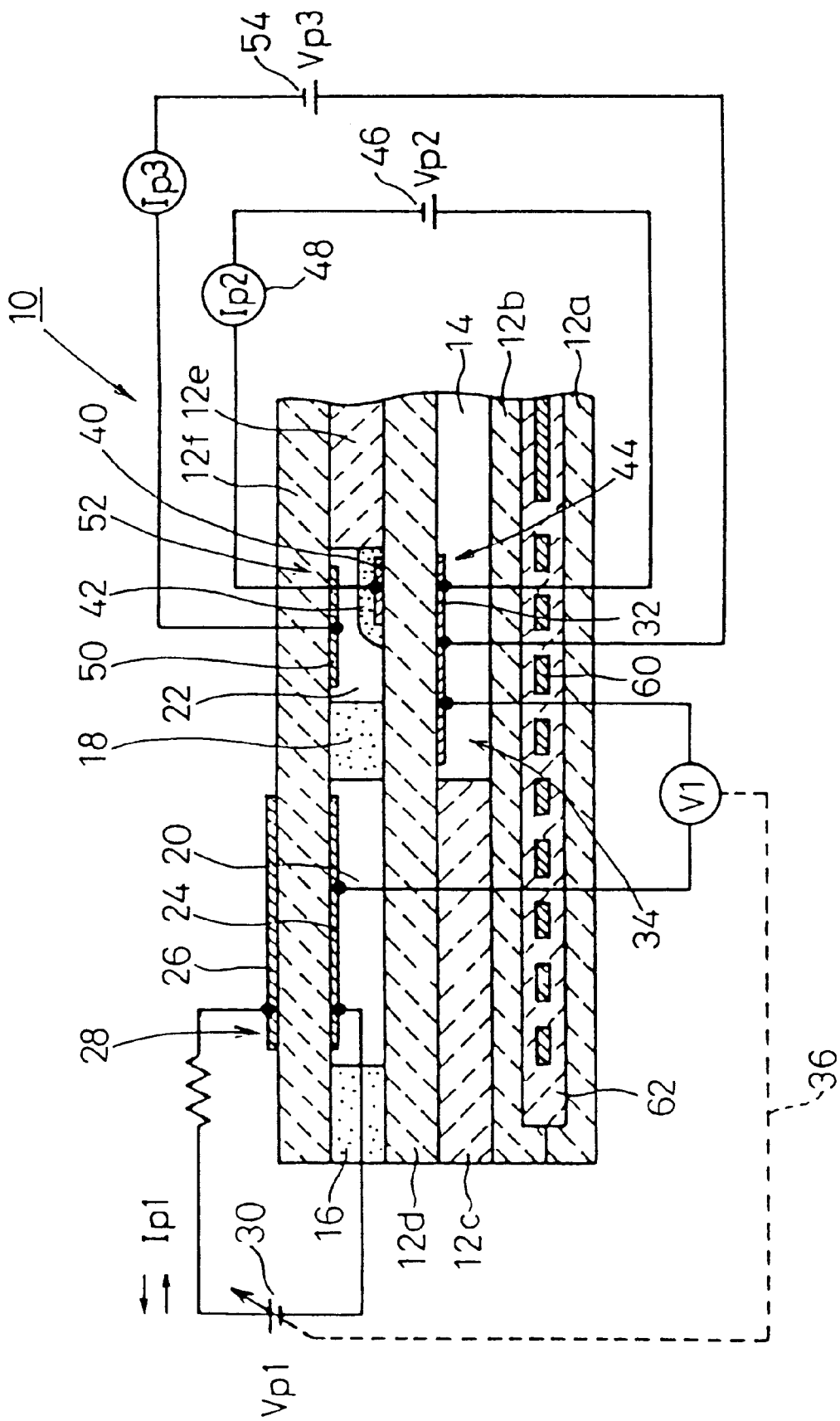
FIG. 1 shows an arrangement of a NOx sensor according to an embodiment of the present invention.

At first, as shown in FIG. 1, a NOx sensor 10 according to the embodiment of the present invention comprises, for example, six stacked solid electrolyte layers 12a to 12f composed of ceramics based on the use of oxygen ion-conductive solid electrolytes such as $ZrO_2$. First and second layers from the bottom are designated as first and second substrate layers 12a, 12b respectively. Third and fifth layers from the bottom are designated as first and second spacer layers 12c, 12e respectively. Fourth and sixth layers from the bottom are designated as first and second solid electrolyte layers 12d, 12f respectively.

Specifically, the first spacer layer 12c is stacked on the second substrate layer 12b. The first solid electrolyte layer 12d, the second spacer layer 12e, and the second solid electrolyte layer 12f are successively stacked on the first spacer layer 12c.

A space (reference gas-introducing space) 14, into which a reference gas such as atmospheric air to be used as a reference for measuring oxides is introduced, is formed between the second substrate layer 12b and the first solid electrolyte layer 12d, the space 14 being comparted by a lower surface of the first solid electrolyte layer 12d, an upper surface of the second substrate layer 12b, and side surfaces of the first spacer layer 12c.

The second spacer layer 12e is interposed between the first and second solid electrolyte layers 12d, 12f. First and second diffusion rate-determining sections 16, 18 are also interposed between the first and second solid electrolyte layers 12d, 12f.

A first chamber 20 for adjusting the partial pressure of oxygen in a measurement gas is formed and comparted by a lower surface of the second solid electrolyte layer 12f, side surfaces of the first and second diffusion rate-determining sections 16, 18, and an upper surface of the first solid electrolyte layer 12d. A second chamber 22 for finely adjusting the partial pressure of oxygen in the measurement gas and measuring oxides, for example, nitrogen oxides (NOx) in the measurement gas is formed and comparted by a lower surface of the second solid electrolyte layer 12f, a side surface of the second diffusion rate-determining section 18, a side surface of the second spacer layer 12e, and an upper surface of the first solid electrolyte layer 12d.

The external space communicates with the first chamber 20 via the first diffusion rate-determining section 16, and the first chamber 20 communicates with the second chamber 22 via the second diffusion rate-determining section 18.

The first and second diffusion rate-determining sections 16, 18 give predetermined diffusion resistances to the measurement gas to be introduced into the first and second chambers 20, 22 respectively. Each of the first and second diffusion rate-determining sections 16, 18 can be formed as a passage composed of, for example, a porous material, or a small hole having a predetermined cross-sectional area so that the measurement gas may be introduced.

Especially, a porous material composed of, for example, $ZrO_2$ is charged and arranged in the second diffusion rate-determining section 18. The diffusion resistance of the second diffusion rate-determining section 18 is made larger than the diffusion resistance of the first diffusion rate-determining section 16. The diffusion resistance of the second diffusion rate-determining section 18 is preferably larger than that of the first diffusion rate-determining section 16. However, no problem occurs even when the former is smaller than the latter.

The atmosphere in the first chamber 20 is introduced into the second chamber 22 under the predetermined diffusion resistance via the second diffusion rate-determining section 18.

An inner pumping electrode 24 having a substantially rectangular planar configuration and composed of a porous cermet electrode (for example, a cermet electrode composed of Pt•$ZrO_2$ containing 1% by weight of Au) is formed on the entire lower surface portion for forming the first chamber 20, of the lower surface of the second solid electrolyte layer 12f. An outer pumping electrode 26 is formed on a portion corresponding to the inner pumping electrode 24, of the upper surface of the second solid electrolyte layer 12f. An electrochemical pumping cell, i.e., a main pumping cell 28 is constructed by the inner pumping electrode 24, the outer pumping electrode 26, and the second solid electrolyte layer 12f interposed between the both electrodes 24, 26.

A desired control voltage (pumping voltage) Vp1 is applied between the inner pumping electrode 24 and the outer pumping electrode 26 of the main pumping cell 28 by the aid of an external variable power source 30 to allow a pumping current Ip1 to flow in a positive or negative direction between the outer pumping electrode 26 and the inner pumping electrode 24. Thus, the oxygen in the atmosphere in the first chamber 20 can be pumped out to the external space, or the oxygen in the external space can be pumped into the first chamber 20.

A reference electrode 32 is formed on a lower surface portion exposed to the reference gas-introducing space 14, of the lower surface of the first solid electrolyte layer 12d. An electrochemical sensor cell, i.e., a controlling oxygen partial pressure-detecting cell 34 is constructed by the inner pumping electrode 24, the reference electrode 32, the second solid electrolyte layer 12f, the second spacer layer 12e, and the first solid electrolyte layer 12d.

The controlling oxygen partial pressure-detecting cell 34 is operated as follows. That is, an electromotive force is generated between the inner pumping electrode 24 and the reference electrode 32 on the basis of a difference in oxygen concentration between the atmosphere in the first chamber 20 and the reference gas (atmospheric air) in the reference gas-introducing space 14. The partial pressure of oxygen in the atmosphere in the first chamber 20 can be detected by using the electromotive force.

The detected value of the partial pressure of oxygen is used to feedback-control the variable power source 30. Specifically, the pumping action effected by the main pumping cell 28 is controlled by the aid of a feedback control system 36 so that the partial pressure of oxygen in the atmosphere in the first chamber 20 has a predetermined value which is sufficiently low to control the partial pressure of oxygen in the second chamber 22 in the next step.

The feedback control system 36 comprises a circuit to perform feedback control for the pumping voltage Vp1 between the outer pumping electrode 26 and the inner pumping electrode 24 so that the difference (detection voltage V1) between the electric potential of the inner pumping electrode 24 and the electric potential of the reference electrode 32 is at a predetermined voltage level. In this embodiment, the inner pumping electrode 24 is grounded.

Therefore, the main pumping cell 28 pumps out or pumps in oxygen in an amount corresponding to the level of the pumping voltage Vp1, of the measurement gas introduced into the first chamber 20. The oxygen concentration in the first chamber 20 is subjected to feedback control to give a predetermined level by repeating the series of operations described above. In this state, the pumping current Ip1, which flows between the outer pumping electrode 26 and the inner pumping electrode 24, represents the difference between the oxygen concentration in the measurement gas and the controlled oxygen concentration in the first chamber 20. The pumping current Ip1 can be used to measure the oxygen concentration in the measurement gas.

The porous cermet electrode, which constructs each of the inner pumping electrode 24 and the outer pumping electrode 26, is composed of a metal such as Pt and a ceramic such as $ZrO_2$. It is necessary to use a material which has a weak reducing ability or no reducing ability with respect to the NO component in the measurement gas, for the inner pumping electrode 24 disposed in the first chamber 20 to make contact with the measurement gas. It is preferable that the inner pumping electrode 24 is composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

In the NOx sensor 10 according to this embodiment, a detecting electrode 40 having a substantially rectangular planar configuration and composed of a porous cermet electrode is formed at a portion separated from the second diffusion rate-determining section 18, on an upper surface portion for forming the second chamber 22, of the upper surface of the first solid electrolyte layer 12d. An alumina film for constructing a third diffusion rate-determining section 42 is formed to cover the detecting electrode 40. An electrochemical pumping cell, i.e., a measuring pumping cell 44 is constructed by the detecting electrode 40, the reference electrode 32, and the first solid electrolyte layer 12d.

The detecting electrode 40 is composed of a porous cermet comprising zirconia as a ceramic and a metal capable of reducing NOx as the measurement gas component. Accordingly, the detecting electrode 40 functions as a NOx-reducing catalyst for reducing NOx existing in the atmosphere in the second chamber 22. Further, the oxygen in the atmosphere in the second chamber 22 can be pumped out to the reference gas-introducing space 14 by applying a constant voltage Vp2 between the detecting electrode 40 and the reference electrode 32 by the aid of a DC power source 46. The pumping current Ip2, which is allowed to flow in accordance with the pumping action performed by the measuring pumping cell 44, is detected by an ammeter 48. Details of the detecting electrode 40 will be described later on.

The constant voltage (DC) power source 46 can apply a voltage of a magnitude to give a limiting current to the pumping for oxygen produced during decomposition in the measuring pumping cell 44 under the inflow of NOx restricted by the third diffusion rate-determining section 42.

On the other hand, an auxiliary pumping electrode 50 having a substantially rectangular planar configuration and composed of a porous cermet electrode (for example, a cermet electrode composed of Pt•$ZrO_2$ containing 1% by weight of Au) is formed on the entire lower surface portion for forming the second chamber 22, of the lower surface of the second solid electrolyte layer 12f. An auxiliary electrochemical pumping cell, i.e., an auxiliary pumping cell 52 is constructed by the auxiliary pumping electrode 50, the second solid electrolyte layer 12f, the second spacer layer 12e, the first solid electrolyte layer 12d, and the reference electrode 32.

The auxiliary pumping electrode 50 is based on the use of a material having a weak reducing ability or no reducing ability with respect to the NO component contained in the measurement gas, in the same manner as the inner pumping electrode 24 of the main pumping cell 28. In this embodiment, it is preferable that the auxiliary pumping electrode 50 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35% by volume of the entire metal components.

A desired constant voltage Vp3 is applied between the reference electrode 32 and the auxiliary pumping electrode 50 of the auxiliary pumping cell 52 by the aid of an external DC power source 54. Thus, the oxygen in the atmosphere in the second chamber 22 can be pumped out to the reference gas-introducing space 14.

Accordingly, the partial pressure of oxygen in the atmosphere in the second chamber 22 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 28 for the first chamber 20, the change in amount of oxygen introduced into the second chamber 22 is greatly reduced as compared with the change in the measurement gas. Accordingly, the partial pressure of oxygen in the second chamber 22 is accurately controlled to be constant.

Therefore, in the NOx sensor 10 according to the embodiment of the present invention constructed as described above, the measurement gas, which has been controlled for the partial pressure of oxygen in the second chamber 22, is introduced into the detecting electrode 40.

As shown in FIG. 1, the NOx sensor 10 according to this embodiment further comprises a heater 60 for generating heat in accordance with electric power supply from the outside. The heater 60 is embedded in a form of being vertically interposed between the first and second substrate layers 12a, 12b. The heater 60 is provided in order to increase the conductivity of oxygen ions. An insulative layer 62 composed of alumina or the like is formed to cover upper and lower surfaces of the heater 60 so that the heater 60 is electrically insulated from the first and second substrate layers 12a, 12b.

The heater 60 is arranged over the entire portion ranging from the first chamber 20 to the second chamber 22. Accordingly, each of the first chamber 20 and the second chamber 22 is heated to a predetermined temperature. Simultaneously, each of the main pumping cell 28, the controlling oxygen partial pressure-detecting cell 34, and the measuring pumping cell 44 is also heated to a predetermined temperature and maintained at that temperature.

Next, the operation of the NOx sensor 10 according to the embodiment of the present invention will be explained. At first, the forward end of the NOx sensor 10 is disposed in the external space. Accordingly, the measurement gas is introduced into the first chamber 20 under the predetermined diffusion resistance via the first diffusion rate-determining section 16. The measurement gas, which has been introduced into the first chamber 20, is subjected to the pumping action for oxygen, caused by applying the predetermined pumping voltage Vp1 between the outer pumping electrode 26 and the inner pumping electrode 24 which construct the main pumping cell 28. The partial pressure of oxygen is controlled to have a predetermined value, for example, $10^{-7}$ atm. The control is performed by the aid of the feedback control system 36.

The first diffusion rate-determining section 16 serves to limit the amount of diffusion and inflow of oxygen in the measurement gas into the measuring space (first chamber 20) when the pumping voltage Vp1 is applied to the main pumping cell 28 so that the current flowing through the main pumping cell 28 is suppressed.

In the first chamber 20, a state of partial pressure of oxygen is established, in which NOx in the atmosphere is not reduced by the inner pumping electrode 24 in an environment of being heated by the external measurement gas and being heated by the heater 60. For example, a condition of partial pressure of oxygen is formed, in which the reaction of NO→1/2N$_2$+1/2O$_2$ does not occur, because of the following reason. That is, if NOx in the measurement gas (atmosphere) is reduced in the first chamber 20, it is impossible to accurately measure NOx in the second chamber 22 disposed at the downstream stage. In this context, it is necessary to establish a condition in the first chamber 20 in which NOx is not reduced by the component which participates in reduction of NOx (in this case, the metal component of the inner pumping electrode 24). Specifically, as described above, such a condition is achieved by using, for the inner pumping electrode 24, the material having a low ability to reduce NOx, for example, an alloy of Au and Pt.

The gas in the first chamber 20 is introduced into the second chamber 22 under the predetermined diffusion resistance via the second diffusion rate-determining section 18. The gas, which has been introduced into the second chamber 22, is subjected to the pumping action for oxygen, caused by applying the voltage Vp3 between the reference electrode 32 and the auxiliary pumping electrode 50 which constitute the auxiliary pumping cell 52 to make fine adjustment so that the partial pressure of oxygen has a constant and low value of partial pressure of oxygen.

The second diffusion rate-determining section 18 serves to limit the amount of diffusion and inflow of oxygen in the measurement gas into the measuring space (second chamber 22) when the voltage Vp3 is applied to the auxiliary pumping cell 52 so that the pumping current Ip3 flowing through the auxiliary pumping cell 52 is suppressed, in the same manner as performed by the first diffusion rate-determining section 16.

The measurement gas, which has been controlled for the partial pressure of oxygen in the second chamber 22 as described above, is introduced into the detecting electrode 40 under the predetermined diffusion resistance via the third diffusion rate-determining section 42.

When it is intended to control the partial pressure of oxygen in the atmosphere in the first chamber 20 to have a low value of the partial pressure of oxygen which does not substantially affect the measurement of NOx, by operating the main pumping cell 28, in other words, when the pumping voltage Vp1 of the variable power source 30 is adjusted by the aid of the feedback control system 36 so that the voltage V1 detected by the oxygen partial pressure-detecting cell 34 is constant, if the oxygen concentration in the measurement gas greatly changes, for example, in a range of 0 to 20%, then the respective partial pressures of oxygen in the atmosphere in the second chamber 22 and in the atmosphere in the vicinity of the detecting electrode 40 slightly change in ordinary cases. This phenomenon is caused probably because of the following reason. That is, when the oxygen concentration in the measurement gas increases, the distribution of the oxygen concentration occurs in the widthwise direction and in the thickness direction in the first chamber 20. The distribution of the oxygen concentration changes depending on the oxygen concentration in the measurement gas.

However, in the case of the NOx sensor 10 according to this embodiment, the auxiliary pumping cell 52 is provided for the second chamber 22 so that the partial pressure of oxygen in its internal atmosphere always has a constant low value of the partial pressure of oxygen. Accordingly, even when the partial pressure of oxygen in the atmosphere introduced from the first chamber 20 into the second chamber 22 changes depending on the oxygen concentration in the measurement gas, the partial pressure of oxygen in the atmosphere in the second chamber 22 can be always made to have a constant low value, owing to the pumping action performed by the auxiliary pumping cell 52. As a result, the partial pressure of oxygen can be controlled to have a low value at which the measurement of NOx is not substantially affected.

NOx in the measurement gas introduced into the detecting electrode 40 is reduced or decomposed around the detecting electrode 40. Thus, for example, a reaction of NO→1/2N$_2$+ 1/2O$_2$ is allowed to occur. In this process, a predetermined voltage Vp2, for example, 430 mV (700° C.) is applied between the detecting electrode 40 and the reference electrode 32 which construct the measuring pumping cell 44, in a direction to pump out the oxygen from the second chamber 22 to the reference gas-introducing space 14.

Therefore, the pumping current Ip2 flowing through the measuring pumping cell 44 has a value which is proportional to a sum of the oxygen concentration in the atmosphere introduced into the second chamber 22, i.e., the oxygen concentration in the second chamber 22 and the oxygen concentration produced by reduction or decomposition of NOx by the aid of the detecting electrode 40.

In this embodiment, the oxygen concentration in the atmosphere in the second chamber 22 is controlled to be constant by means of the auxiliary pumping cell 52. Accordingly, the pumping current Ip2 flowing through the measuring pumping cell 44 is proportional to the NOx concentration. The NOx concentration corresponds to the amount of diffusion of NOx limited by the third diffusion rate-determining section 42. Therefore, even when the oxygen concentration in the measurement gas greatly changes, it is possible to accurately measure the NOx concentration, based on the use of the measuring pumping cell 44 by the aid of the ammeter 48.

According to the fact described above, almost all of the pumping current value Ip2 obtained by operating the measuring pumping cell 44 represents the amount brought about by the reduction or decomposition of NOx. Accordingly, the obtained result does not depend on the oxygen concentration in the measurement gas.

The detecting electrode 40, which is formed in the second chamber 22, will now be described in detail below. For example, when a cermet electrode composed of $Rh/ZrO_2$ was used for the detecting electrode 40, a phenomenon was observed, in which the sensitivity was lowered in accordance with the increase in operating time.

This phenomenon was caused by the increase in impedance of the measuring pumping cell 44. When the NOx sensor 10, in which the impedance had been increased, was observed, it was found that the contact area was decreased between the detecting electrode 40 and the first solid electrolyte layer 12d. In other words, it is postulated that the increase in impedance is caused by the decrease in contact area between the detecting electrode 40 and the first solid electrolyte layer 12d.

Accordingly, an experiment (conveniently referred to as "first illustrative experiment") was carried out. In this experiment, the way of change of the mass of the alloy composed of Pt and Rh depending on the increase in heat was measured by using a thermo-balance while changing the weight ratio between Pt and Rh. Obtained results are shown in FIG. 2.

Figure 2:
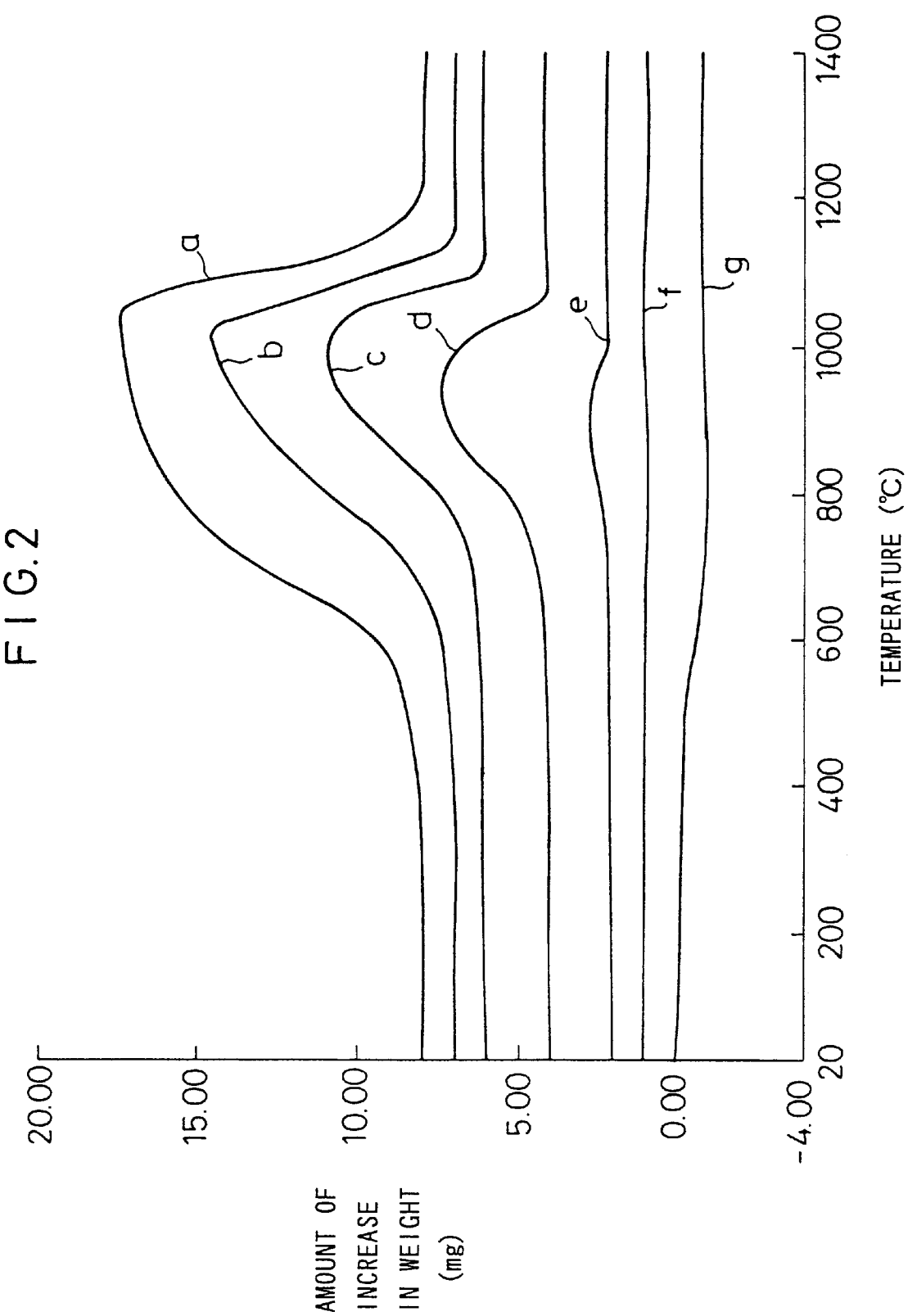
FIG. 2 shows characteristics illustrating results of a first illustrative experiment (illustrative experiment to measure the way of change in mass of alloys composed of Rh and Pt, in accordance with the increase in heat, by changing the weight ratio of Rh and Pt)

In FIG. 2, a curve "a" represents a characteristic obtained for Pt/Rh=0/100% by weight. A curve "b" represents a characteristic obtained for Pt/Rh=10/90% by weight. A curve "c" represents a characteristic obtained for Pt/Rh=25/75% by weight. A curve "d" represents a characteristic obtained for Pt/Rh=50/50% by weight. A curve "e" represents a characteristic obtained for Pt/Rh=75/25% by weight. A curve "f" represents a characteristic obtained for Pt/Rh=90/10% by weight. A curve "g" represents a characteristic obtained for Pt/Rh=100/0% by weight.

According to the experimental results shown in FIG. 2, the following fact is understood. That is, in the case of Pt/Rh=0/100% by weight, the increase in weight, which is caused by oxidation of Rh ($Rh_2O_3$), is observed from about 600° C. to about 1080° C. The conversion into the metal is started again from about 1080° C., and the weight is decreased. The original weight is restored in the vicinity of about 1200° C.

Similarly, the following fact is understood. That is, in the case of Pt/Rh=10/90% by weight, the increase in weight, which is caused by oxidation of Rh ($Rh_2O_3$), is observed from about 700° C. to about 1020° C. The conversion into the metal is started again from about 1020° C., and the weight is decreased. The original weight is restored in the vicinity of about 1140° C.

The following Table 1 summarizes the range of the increase in weight due to the oxidation as described above, the range of the decrease in weight due to the reconversion into the metal, and the span of the change in weight.

TABLE 1

| Pt/Rh | Temperature range for increase in weight | Temperature range for decrease in weight | Span of change in weight |
|---|---|---|---|
| 0/100 wt % | about 600° C. to about 1080° C. | about 1080° C. to about 1200° C. | about 9.5 mg |
| 10/90 wt % | about 700° C. to about 1020° C. | about 1020° C. to about 1140° C. | about 7.5 mg |
| 25/75 wt % | about 800° C. to about 1000° C. | about 1000° C. to about 1100° C. | about 5.0 mg |
| 50/50 wt % | about 800° C. to about 960° C. | about 960° C. to about 1070° C. | about 3.5 mg |
| 75/25 wt % | about 840° C. to about 920° C. | about 920° C. to about 1000° C. | about 1.0 mg |
| 90/10 wt % | no increase in weight | no decrease in weight | 0 mg |
| 100/0 wt % | no increase in weight | about 600° C. to about 800° C. | about −1 mg |

Figure 3:
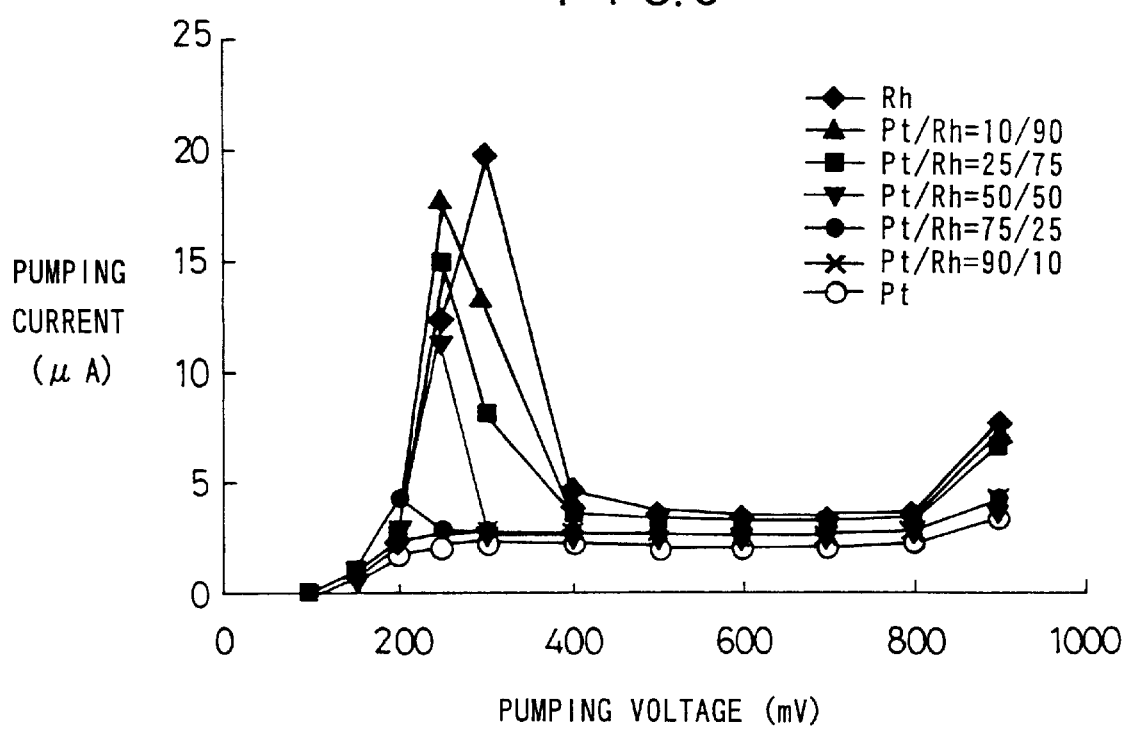
FIG. 3 shows limiting current characteristics obtained upon application of heating at 800° C. in the atmospheric air in a second illustrative experiment.
Figure 4:
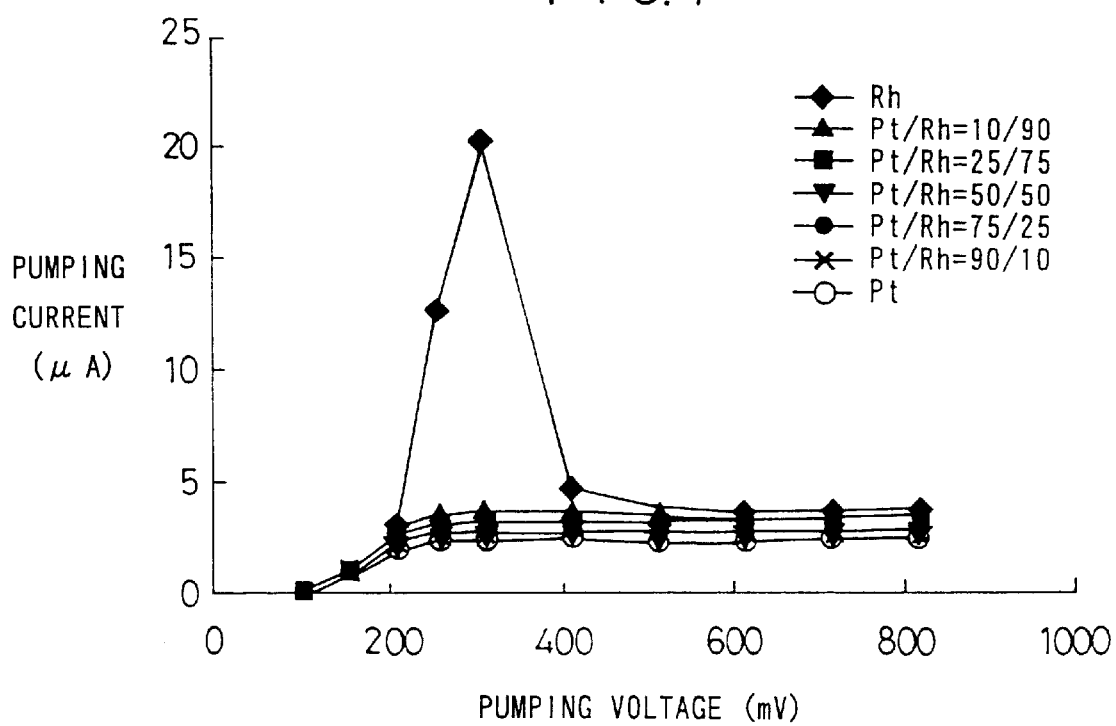
FIG. 4 shows limiting current characteristics obtained upon application of heating at 700° C. in the atmospheric air in the second illustrative experiment.

Another illustrative experiment (conveniently referred to as "second illustrative experiment") was carried out. In this experiment, Pt and Rh were contained in the detecting electrode 40 in the seven ratios of Pt/Rh described above to produce NOx sensors 10 respectively. Limiting current characteristics were plotted for the seven types of NOx sensors 10. FIG. 3 shows the limiting current characteristics obtained by applying the heating operation in the atmospheric air at 800° C. FIG. 4 shows the limiting current characteristics obtained by applying the heating operation in the atmospheric air at 700° C.

As for the characteristics shown in FIG. 3, an abnormal pumping current having a peak of about 20 mA passed in the NOx sensor 10 with Pt/Rh=0/100% by weight. An abnormal pumping current having a peak of about 18 mA passed in the NOx sensor 10 with Pt/Rh=10/90% by weight. An abnormal pumping current having a peak of about 15 mA passed in the NOx sensors 10 with Pt/Rh=25/75% by weight and Pt/Rh=50/50% by weight respectively. An abnormal pumping current having a peak of about 4 mA passed in the NOx sensor 10 with Pt/Rh=75/25% by weight.

That is, as shown in FIG. 3, when the heating operation was applied in the atmospheric air at 800° C., the abnormal increase in pumping current was observed at a rate corresponding to the magnitude of the peak value of the increment of the weight shown in FIG. 2. When the heating operation was applied in the atmospheric air at 700° C., the abnormal increase in pumping current was observed only for the NOx sensor 10 having the detecting electrode 40 of Pt/Rh=0/100% by weight. The abnormal increase in pumping current was not observed for the other NOx sensors 10. According to this fact, it is considered that the abnormal increase in pumping current shown in FIGS. 3 and 4 is the increase caused by the pumping action for oxygen originating from the oxide of Rh ($Rh_2O_3$).

When the NOx sensor 10 is practically used, the element temperature is usually set to be about 700° C. Therefore, for example, when the detecting electrode 40 is constructed by a cermet electrode of Rh=100% by weight, the decrease in volume occurs due to the reconversion into the metal of Rh by the oxygen pumping effected by the detecting electrode 40 during the operation of the sensor. Immediately after the operation of the sensor is stopped, the oxygen pumping is stopped, but the element temperature is still not less than 600° C. Therefore, the oxidation of Rh ($Rh_2O_3$) occurs, and the increase in volume of Rh takes place.

The contact area between the detecting electrode 40 and the first solid electrolyte layer 12d is decreased by the repetition of the series of the increase in volume and the decrease in volume. In such a situation, it is postulated that the impedance of the measuring pumping cell 44 is increased, and the sensitivity to NOx is decreased.

Figure 5A:
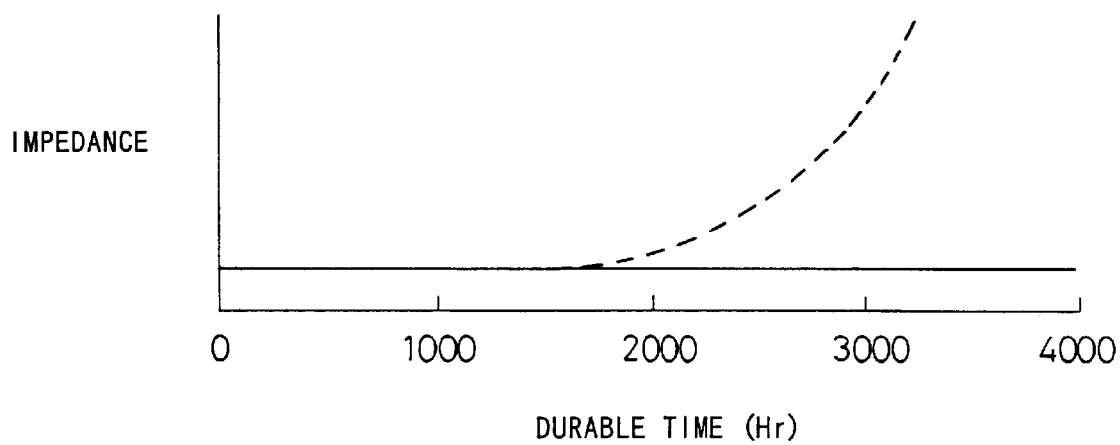
FIG. 5A shows the change in impedance with respect to the durable time in a third illustrative experiment.
Figure 5B:
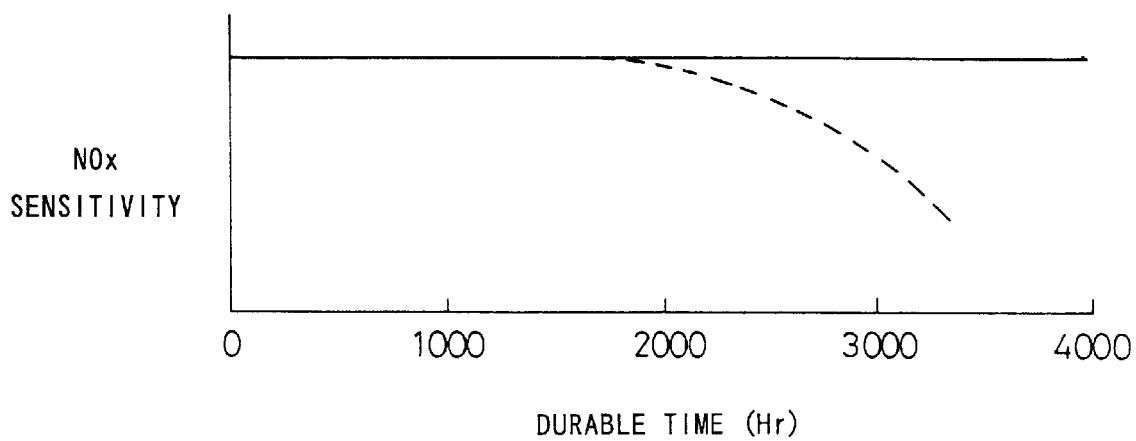
FIG. 5B shows the change in NOx sensitivity with respect to the durable time in the third illustrative experiment.

A still another illustrative experiment (conveniently referred to as "third illustrative experiment") will now be described. In the third illustrative experiment, observation was made for the change in sensitivity to NOx upon practical use of NOx sensors concerning Working and Comparative Examples. In the Working Example, the ratio of Pt/Rh contained in the detecting electrode 40 was 50/50% by weight for the NOx sensor 10 according to the embodiment of the present invention. In the Comparative Example, the ratio of Pt/Rh contained in the detecting electrode 40 was 0/100% by weight. Results of the third illustrative experiment are shown in FIGS. 5A and 5B. In these drawings, the characteristic obtained in the Working Example is depicted by a solid line, and the characteristic obtained in the Comparative Example is depicted by a broken line.

According to the experimental results, the increase in impedance of the measuring pumping cell 44 was started from about 1800 hours in Comparative Example, and the decrease in sensitivity to NOx was observed in accordance with the increase in the impedance. On the other hand, in Working Example, no increase in impedance was observed even after the passage of 4000 hours, and no decrease in sensitivity to NOx was observed as well.

As described above, in the NOx sensor 10 according to the embodiment of the present invention, the cermet electrode, which is composed of the Pt—Rh alloy and the ceramic component, is used as the detecting electrode 40 for constructing the measuring pumping cell 44. Therefore, it is possible to suppress the oxidation of Rh and the reconversion into the metal contained in the detecting electrode 40. Even when the operating time of the NOx sensor 10 is increased, there is no occurrence of the increase in impedance which would be otherwise caused by the decrease in contact area between the detecting electrode 40 and the first solid electrolyte layer 12d. That is, the NOx sensor 10 according to the embodiment of the present invention makes it possible to stabilize the impedance and stabilize the measurement sensitivity.

As also understood from the experimental results described above, the ratio between Pt and Rh contained in the detecting electrode 40 is preferably, in weight ratio, Pt:Rh=10:90 to 90:10, and more preferably Pt:Rh=25:75 to 75:25.

Next, a modified embodiment 10a of the NOx sensor 10 according to the foregoing embodiment will be described with reference to FIG. 6. Components or parts corresponding to those shown in FIG. 1 are designated by the same reference numerals.

Figure 6:
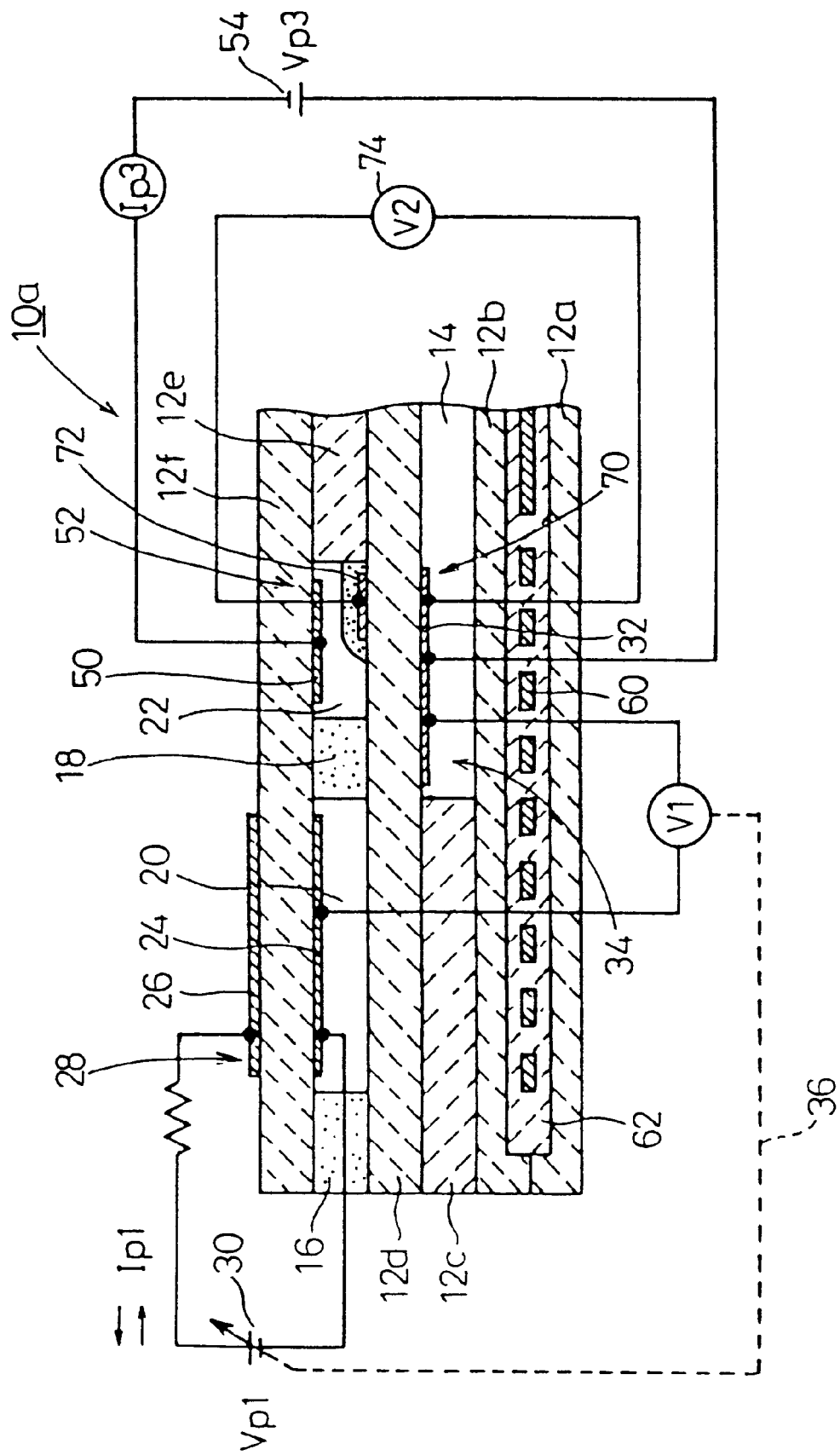
FIG. 6 shows an arrangement of a NOx sensor according to a modified embodiment of the present invention.

As shown in FIG. 6, a NOx sensor 10a according to the modified embodiment is constructed in approximately the same manner as the NOx sensor 10 according to the foregoing embodiment (see FIG. 1). However, the former is different from the latter in that a measuring oxygen partial pressure-detecting cell 70 is provided in place of the measuring pumping cell 44.

The measuring oxygen partial pressure-detecting cell 70 comprises a detecting electrode 72 formed on an upper surface portion for forming the second chamber 22, of the upper surface of the first solid electrolyte layer 12d, the reference electrode 32 formed on the lower surface of the first solid electrolyte layer 12d, and the first solid electrolyte layer 12d interposed between the both electrodes 72, 32.

In this embodiment, an electromotive force (electromotive force of an oxygen concentration cell) V2 corresponding to the difference in oxygen concentration between the atmosphere around the detecting electrode 72 and the atmosphere around the reference electrode 32 is generated between the reference electrode 32 and the detecting electrode 72 of the measuring oxygen partial pressure-detecting cell 70.

Therefore, the partial pressure of oxygen in the atmosphere around the detecting electrode 72, in other words, the partial pressure of oxygen defined by oxygen produced by reduction or decomposition of the measurement gas component (NOx) is detected as a voltage value by measuring the electromotive force (voltage V2) generated between the detecting electrode 72 and the reference electrode 32 by using a voltmeter 74.

Also in the NOx sensor 10a according to the modified embodiment, the cermet electrode, which is composed of the Pt—Rh alloy and the ceramic component, is used as the detecting electrode 72 for constructing the measuring oxygen partial pressure-detecting cell 70. As a result, it is possible to suppress the oxidation of Rh and the reconversion into the metal contained in the detecting electrode 72. Even when the operating time of the NOx sensor 10a is increased, there is no occurrence of the increase in impedance which would be otherwise caused by the decrease in contact area between the detecting electrode 72 and the first solid electrolyte layer 12d. That is, the NOx sensor 10a according to the modified embodiment also makes it possible to stabilize the impedance and stabilize the measurement sensitivity.

It is a matter of course that the NOx concentration-measuring apparatus according to the present invention is not limited to the embodiments described above, which may be embodied in other various formed without deviating from the gist or essential characteristics of the present invention.

As explained above, according to NOx concentration-measuring apparatus concerning the present invention, it is possible to suppress the oxidation of Rh and the reconversion into the metal contained in the NOx-decomposing electrode, stabilize the impedance, and stabilize the measurement sensitivity.

What is claimed is:

1. A method of suppressing oxidation of an Rh-containing cermet electrode in a NOx concentration measuring apparatus while using said apparatus to measure a NOx concentration in a measurement gas, comprising the steps of:
    alloying the electrode with Pt such that a weight ratio of Pt:Rh ranges from 25:75 to 50:50; and
    measuring said NOx concentration in said measurement gas.

* * * * *